United States Patent [19]

Pawloski

[11] 3,975,393

[45] Aug. 17, 1976

[54] CERTAIN 2-PYRIDYL-PHOSPHONAMIDOTHIOATES AND DERIVATIVES THEREOF

[75] Inventor: Chester E. Pawloski, Bay City, Mich.

[73] Assignee: The Dow Chemical Company, Midland, Mich.

[22] Filed: Oct. 6, 1975

[21] Appl. No.: 619,861

Related U.S. Application Data

[63] Continuation of Ser. No. 468,847, May 10, 1974, abandoned.

[52] U.S. Cl. .................. 260/294.8 K; 260/296 R; 424/263
[51] Int. Cl.² ........................................ C07D 213/52
[58] Field of Search ............... 260/294.8 K, 296 R, 260/297 P; 424/200

[56] References Cited
UNITED STATES PATENTS 3,743,643  7/1973  Rigterink ................. 260/294.8 K

*Primary Examiner*—Alan L. Rotman
*Attorney, Agent, or Firm*—Edward E. Schilling

[57] ABSTRACT

Substituted pyridinyl-(2)-phosphoramidates and -phosphonamidothioates are disclosed which are useful as insecticides. The compounds are prepared by the reaction of selected substituted pyridinol and phosphonamido-chloridate or chloridothioate reactants.

14 Claims, No Drawings

CERTAIN 2-PYRIDYL-PHOSPHONAMIDOTHIOATES AND DERIVATIVES THEREOF

CROSS-REFERENCE TO RELATED APPLICATION

This is a continuation, of application Ser. No. 468,847 filed May 10, 1974, now abandoned.

SUMMARY OF THE INVENTION

The present invention relates to certain novel substituted pyridinyl-(2)-phosphonamidates and -phosphonamidothioates, hereinafter referred to for convenience as "active ingredients." The active ingredients of the present invention are those of the following general formula:

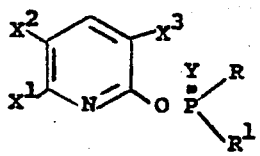

wherein
Y represents a chalcogen of atomic number 8 to 16, inclusive;
each of $X^1$, $X^2$ and $X^3$ independently represents hydrogen, bromo, chloro, fluoro or trifluoromethyl, with the proviso that at least one of $X^1$, $X^2$ and $X^3$ is always other than hydrogen;
R represents an alkyl radical;
$R^1$ represents

$R^2$ and $R^3$ each independently represent hydrogen, methyl or ethyl;
the active ingredients are useful as pesticides in the control of various insect organisms.

DETAILED DESCRIPTION OF THE INVENTION

The term "alkyl" as used herein means a straight- or branched-chain radical containing from one to about three carbon atoms, such as, for example, methyl, ethyl, propyl and the like. The term "chalcogen" means those members of the recognized chalcogen group having an atomic number of 8–16, inclusive, i.e., oxygen and sulfur. The term "halo" or "halogen", where employed herein, means bromo, chloro or fluoro.

The active ingredients of the present invention are usually oily liquids at ambient temperatures and are soluble in organic solvents such as, for example, carbon tetrachloride, acetone, toluene, methylene chloride, dimethylformamide and the like. The active ingredients of the above formula wherein R represents alkyl constitute a preferred embodiment of the present invention. In still another embodiment of the present invention, active ingredients wherein at least one of $R^2$ and $R^3$ is hydrogen are preferred. Still another preferred class of active ingredients are those of the above formula wherein R is alkyl, Y is sulfur and $X^2$ and $X^3$ each represent hydrogen. An especially preferred group of compounds include those selected from the group consisting of:

O-(6-chloro-2-pyridinyl) P-ethyl N-methylphosphonamidothioate,
O-(6-chloro-2-pyridinyl) P-methyl N-methylphosphonamidothioate,
O-(6-chloro-2-pyridinyl) P-ethylphosphonamidothioate,
O-(6-fluoro-2-pyridinyl) P-ethyl N-methylphosphonamidothioate,
O-(5-chloro-2-pyridinyl) P-ethyl N-methylphosphonamidothioate,
O-(3,5,6-trichloro-2-pyridinyl) P-ethyl N-methylphosphonamidothioate,
O-(5-bromo-3,6-dichloro-2-pyridinyl) P-ethyl N-methylphosphonamidothioate, and
O-(6-(trifluoromethyl)-2-pyridinyl) P-ethyl N-methylphosphonamidothioate.

The active ingredients of the present invention are prepared by reacting a substituted 2-pyridinol or the alkaline salt thereof with a selected substituted phosphonamido chloridate or phosphonamido chloridothioate. The reaction is preferably carried out in the presence of an inert carrier medium and can be schematically illustrated as follows:

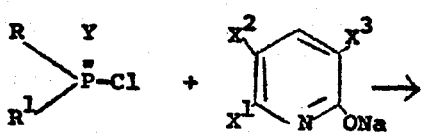

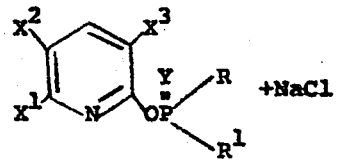

wherein all substituents are as previously defined. Representative carrier mediums include, for example, benzene, toluene, xylene, acetone, methylisopropyl ketone, methylisobutyl ketone, acetonitrile, dimethyl formamide, methylene chloride and the like. The reaction is further preferably carried out in the presence of an acid acceptor. For this purpose, the customary acid-binding agents can be employed. Those that are particularly suitable include, for example, alkali metal alcoholates and carbonates; such as potassium and sodium methylate or ethylate, sodium and potassium carbonate and tertiary amines such as, for example, triethylamine, dimethylaniline, pyridine and the like. A small amount of a catalyst, such as mercurous chloride, preferably trimethylbenzylammonium chloride, and the like is also preferably employed.

Ordinarily, a solution or suspension of a salt of the substituted 2-pyridinol reactant is first prepared and this is subsequently reacted with agitation with an appropriate phosphonamido chloridate or phosphonamido chloridothioate. The reactants, as well as the auxiliary substances (acid-acceptors), are, in general, employed in stoichiometric amounts. The reaction temperature can be varied over a fairly wide range and, in general, the reaction is carried out at temperatures of from about 0° to about 50°C. Generally, the reaction is carried out for a period of from about 1 to about 8 hours. The crude product is usually obtained in the form of a viscous oil which can be freed from volatile impurities by heating at moderately elevated temperatures under reduced pressure. The refractive index can be used as a more precise determination of the product characterization.

The following non-limitative examples further illustrate the invention.

EXAMPLE 1

38.0 grams (0.25 mole) of the sodium salt of 6-chloro-2-pryidinol, 39.0 grams (0.25 mole) of N-methyl ethylphosphonamido chloridothioate and 0.4 gram of $HgCl_2$ were mixed with 300 milliliters (ml.) of acetonitrile. The resulting reaction mixture was heated to about 40°–45°C. for about 2 hours and then allowed to cool, the reaction mixture was subsequently filtered and the solvent removed under reduced pressure at 40°C. The resulting residual oil was dissolved in about 250 ml. of methylene chloride and the resulting mixture was mixed with about 250 ml. of 2% sodium hydroxide solution for a period of about 15 minutes. Following this period, the organic product layer of the mixture was separated, washed with two 150 ml. portions of water, again separated and dried over sodium sulfate. The product layer was filtered and distilled under reduced pressure to remove the solvent carrier. As a result of such operations, the desired O-(6-chloro-2-pyridinyl) P-ethyl N-methylphosphonamidothioate product was recovered as an oil having a refractive index of $n_D^{25°C} = 1.5696$. Infrared and nuclear magnetic resonance spectra supported the structure of the product.

Other active ingredients of the present invention are similarly prepared according to the teachings of the specification and the foregoing example by employing the appropriate pyridinol and phosphono-chlorides or chloridothioates. Such other active ingredients include the following:

O-(6-chloro-2-pyridinyl) P-methyl N-methylphosphonamidothioate, having a refractive index $n_D^{25°C} = 1.5813$;

O-(6-chloro-2-pyridinyl) P-ethylphosphonamidothioate, having a refractive index $n_D^{25°C} = 1.5765$;

O-(6-fluoro-2-pyridinyl) P-ethyl N-methylphosphonamidothioate;

O-(5-chloro-2-pyridinyl) P-ethyl N-methylphosphonamidothioate, having a refractive index $n_D^{25°C} = 1.5749$;

O-(3,5,6-trichloro-2-pyridinyl) P-ethyl N-methylphosphonamidothioate, having a refractive index $n_D^{25°C} = 1.5480$;

O-(5-bromo-3,6-dichloro-2-pyridinyl) P-ethyl N-methylphosphonamidothioate, having a melting point of 75°–78°C.;

O-(6-(trifluoromethyl)-2-pyridinyl) P-ethyl N-methylphosphonamidothioate, having a refractive index $n_D^{25°C} = 1.5043$;

O-(3,5-dibromo-2-pyridinyl) P-3,5-dichlorophenyl N-ethylphosphonamidothioate;

O-(3,6-bis(trifluoromethyl)-2-pyridinyl) P-propyl N-dimethylphosphonamidothioate;

O-(3-chloro-2-pyridinyl) P-phenyl N-diethylphosphonamidothioate;

O-(3,5,6-tribromo-2-pyridinyl) P-4-ethylphenyl N-methylphosphonamidothioate;

O-(3,5-difluoro-2-pyridinyl) P-ethyl N-methylphosphonamidothioate; and

O-(6-bromo-3-chloro-2-pyridinyl) P-propyl N-methylphosphonamidothioate.

The corresponding phosphonate derivatives of the above-named compounds are similarly prepared by employing the corresponding substituted phosphonchloridate reactants. Other substituted pyridinyl-(2)-phosphonamidates and -phosphonamidothioates within the scope of the present invention can also be prepared according to the foregoing teachings and examples.

The active ingredients of the present invention are useful in the control of various pest organisms such as, for example, Codling moth, two-spotted spider mites, ticks, house flies and the like. The corresponding phosphonate derivatives of the above-named compounds are similarly prepared by employing the corresponding substituted phosphonochloridate reactants. Other substituted pyridine phosphonates and phosphonothioate compounds within the scope of the present invention can also be prepared according to the foregoing teachings and examples.

The active ingredients of the present invention have been found to possess good activity against cotton leafworm larvae (*Spodoptera littoralis Boisd.*). Accordingly, the present invention also comprises methods for controlling cotton leafworm larvae by contacting such organisms and/or their habitates with a pesticidally effective amount of one or more active ingredients. For such uses, unmodified active ingredients of the present invention can be employed. However, the present invention embraces the use of a pesticidally effecitve amount of the active ingredients in composition form with an inert material known in the art as an adjuvant or carrier in solid or liquid form. Thus, for example, an active ingredient can be dispersed on a finely divided solid and employed therein as a dust. Also, the active ingredients, as liquid concentrates or solid compositions comprising one or more of the active ingredients, can be dispersed in water, typically with the aid of a wetting agent, and the resulting aqueous dispersion employed as a spray. In other procedures, the active ingredient can be employed as a constituent of organic liquid compositions, oil-in-water and water-in-oil emulsions, or water dispersions, with or without the addition of wetting, dispersing, or emulsifying agents. Suitable adjuvants of the foregoing type are well known to those skilled in the art. The methods of applying the solid or liquid pesticidal formulations similarly are well known to the skilled artisan.

As organic solvents used as extending agents there can be employed hydrocarbons, e.g., benzene, toluene, xylene, kerosene, diesel fuel, fuel oil, and petroleum naphtha, ketones such as acetone, methyl ethyl ketone and cyclohexanone, chlorinated hydrocarbons such as carbon tetrachloride, chloroform, trichloroethylene, and perchloroethylene, esters such as ethyl acetate, amyl acetate and butyl acetate, ethers, e.g., ethylene glycol monomethyl ether and diethylene glycol monomethyl ether, alcohols, e.g., methanol, ethanol, isopropanol, amyl alcohol, ethylene glycol, propylene glycol, butyl Carbitol acetate and glycerine. Mixtures of water and organic solvents, either as solutions or emulsions, can be employed.

The active ingredients can also be applied as aerosols, e.g., by dispersing them in air by means of a compressed gas such as dichlorodifluoromethane or trichlorofluoromethane and other Freons and Genetrons, for example.

The active ingredients of the present invention can also be applied with adjuvants or carriers such as talc, pyrophyllite, synthetic fine silica, attapulgus clay, kieselguhr, chalk, diatomaceous earth, lime, calcium carbonate, bentonite, fuller's earth, cottonseed hulls, wheat flour, soybean flour, pumice, tripoli, wood flour, walnut shell flour, redwood flour and lignin.

As stated, it is frequently desirable to incorporate a surface active agent in the compositions of the present invention. Such surface active or wetting agents are advantageously employed in both the solid and liquid compositions. The surface active agent can be anionic, cationic or nonionic in character.

Typical classes of surface active agents include alkyl sulfonate salts, alkylaryl sulfonate salts, alkylaryl polyether alcohols, fatty acid esters of polyhydric alcohols and the alkylene oxide addition products of such esters, and addition products of long chain mercaptans and alkylene oxides. Typical examples of such surface active agents include the sodium alkylbenzene sulfonates having 10 to 18 carbon atoms in the alkyl group, alkylphenol ethylene oxide condensation products, e.g., p-isooctylphenol condensed with 10 ethylene oxide units, soaps, e.g., sodium stearate and potassium oleate, sodium salt of propylnaphthalene sulfonic acid, di(2-ethylhexyl)-ester of sodium sulfosuccinic acid, sodium lauryl sulfate, sodium decant sulfonate, sodium salt of the sulfonated monoglyceride of coconut fatty acids, sorbitan sesquioleate, lauryl trimethyl ammonium chloride, octadecyl trimethyl ammonium chloride, polyethylene glycol lauryl ether, polyethylene glycol esters of fatty acids and rosin acids, e.g., Ethofat 7 and 13, sodium N-methyl-N-oleyl taurate, Turkey Red Oil, sodium dibutyl naphthalene slfonate, sodium lignin sulfonate, polyethylene glycol stearate, sodium dodecylbenzene sulfonate, tertiary dodecyl polyethylene glycol thioether (nonionic 218), long chain ethylene oxide-propylene oxide condensation products, e.g., Pluronic 61 (molecular weight 1000), polyethylene glycol ester of tall oil acids, sodium octyl phenoxyethoxyethyl sulfate, tris(polyoxyethylene)-sorbitan monostearate (Tween 60), and sodium dihexyl sulfosuccinate.

The concentration of the active ingredients in liquid compositions generally is from about 0.01 to about 95 percent by weight or more. Concentrations of from about 0.1 to about 50 weight percent are often employed. In dusts or dry formulations, the concentration of the active ingredient can be from about 0.01 to about 95 percent or more; concentrations of from about 0.1 to about 50 weight percent are often conveniently employed. In compositions to be employed as concentrates, the active ingredient can be present in a concentration of from about 5 to about 98 weight percent. The active ingredient compositions can also contain other compatible additaments, for example, plant growth regulants, pesticides and the like.

For such uses, unmodified active ingredients of the present invention can be employed. However, the present invention embraces the use of a pesticidally effective amount of the active ingredients in composition form with an inert material known in the art as an adjuvant or carrier in solid or liquid form. Thus, for example, an active ingredient can be dispersed on a finely divided solid and employed therein as a dust. Also the active ingredients, as liquid concentrates or solid compositions comprising one or more of the active ingredients, can be dispersed in water, typically with the aid of a wetting agent, and the resulting aqueous dispersion employed as a spray. In other procedures, the active ingredient can be employed as a constituent of organic liquid compositions, oil-in-water and water-in-oil emulsions, or water dispersions, with or without the addition of wetting, dispersing, or emulsifying agents.

Suitable adjuvants of the foregoing type are well known to those skilled in the art. The methods of applying the solid or liquid pesticidal formulations similarly are well known to the skilled artisan.

As organic solvents used as extending agents there can be employed hydrocarbons, e.g., benzene, toluene, xylene, kerosene, diesel fuel, fuel oil, and petroleum naphtha, ketones such as acetone, methyl ethyl ketone and cyclohexanone, chlorinated hydrocarbons such as carbon tetrachloride, chloroform, trichloroethylene, and perchloroethylene, esters such as ethyl acetate, amyl acetate and butyl acetate, ethers, e.g., ethylene glycol monomethyl ether and diethylene glycol monomethyl ether, alcohols, e.g., methanol, ethanol, isopropanol, amyl alcohol, ethylene glycol, propylene glycol, butyl Carbitol acetate and glycerine. Mixtures of water and organic solvents, either as solutions or emulsions, can be employed.

The active ingredients can also be applied as aerosols, e.g., by dispersing them in air by means of a compressed gas such as dichlorodifluoromethane or trichlorofluoromethane and other Freons and Genetrons, for example.

The active ingredients of the present invention can also be applied with adjuvants or carriers such as talc, pyrophyllite, synthetic fine silica, attapulgus clay, kieselguhr, chalk, diatomaceous earth, lime, calcium carbonate, bentonite, fuller's earth, cottonseed hulls, wheat flour, soybean flour, pumice, tripoli, wood flour, walnut shell flour, redwood flour and lignin.

As stated, it is frequently desirable to incorporate a surface active agent in the compositions of the present invention. Such surface active or wetting agents are advantageously employed in both the solid and liquid compositions. The surface active agent can be anionic, cationic or nonionic in character.

Typical classes of surface active agents include alkyl sulfonate salts, alkylaryl sulfonate salts, alkylaryl polyether alcohols, fatty acid esters of polyhydric alcohols and the alkylene oxide addition products of such esters, and addition products of long chain mercaptans and alkylene oxides.

Typical examples of such surface active agents include the sodium alkylbenzene sulfonates having 10 to 18 carbon atoms in the alkyl group, alkylphenol ethylene oxide condensation products, e.g., p-isooctylphenol condensed with 10 ethylene oxide units, soaps, e.g., sodium stearate and potassium oleate, sodium salt of propylnaphthalene sulfonic acid, di(2-ethylhexyl)ester of sodium sulfosuccinic acid, sodium lauryl sulfate, sodium decane sulfonate, sodium salt of the sulfonated monoglyceride of coconut fatty acids, sorbitan sesquioleate, lauryl trimethyl ammonium chloride, octadecyl trimethyl ammonium chloride, polyethylene glycol lauryl ether, polyethylene glycol esters of fatty acids and rosin acids, e.g., Ethofat 7 and 13, sodium N-methyl-N-oleyl taurate, Turkey Red Oil, sodium dibutyl naphthalene sulfonate, sodium lignin sulfonate, polyethylene glycol stearate, sodium dodecylbenzene sulfonate, tertiary dodecyl polyethylene glycol thioether (nonionic 218), long chain ethylene oxide-propylene oxide condensation products, e.g., Pluronic 61 (molecular weight 1000), polyethylene glycol ester of tall oil acids, sodium octyl phenoxyethoxyethyl sulfate, tris(-polyoxyethylene)sorbitan monostearate (Tween 60), and sodium dihexyl sulfosuccinate.

The concentration of the active ingredients in liquid compositions generally is from about 0.01 to about 95 percent by weight or more. Concentrations of from about 0.1 to about 50 weight percent are often employed. In dusts or dry formulations, the concentration of the active ingredient can be from about 0.01 to about 95 weight percent or more; concentrations of from about 0.1 to about 50 weight percent are often conveniently employed. In compositions to be employed as concentrates, the active ingredient can be present in a concentration of from about 5 to about 98 weight percent. The active ingredient compositions can also contain other compatible additaments, for example, plant growth regulants, pesticides and the like.

The present compositions can be applied by the use of power-dusters, boom and hand sprayers, spray-dusters and by other conventional means. The compositions can also be applied from airplanes as a dust or a spray.

The exact dosage to be applied is dependent upon the specific active ingredient being employed and it is to be understood that all of the active ingredients of the invention and compositions containing the same may not be equally effective at similar concentrations or against the same insects. The method of application as well as the particular insect to be controlled are further factors to be considered in determining the exact dosage rate. In view of the foregoing and following disclosures, one skilled in the art can readily determine the optimum rate to be applied in any particular case.

So as to illustrate the properties of the active ingredients in the control of insects, a group of controlled experiments is described below with representative active ingredients of the present invention.

EXAMPLE 2

Host Cranberry bean plants infested with from 50 to 100 two-spotted spider mites, (*Tetranychus bimaculatus* Harvey) are dipped in aqueous dispersions containing one of the active ingredients of the present invention at a concentration of 400 parts per million (p.p.m.). An additional quantity of the test ingredient solution (approximately 0.2016/Acre) is applied to the soil in the root area of the plants. The plants are then maintained under conditions conducive to the growth of the plants and mites. The plants are checked 6 days following the application of the test ingredient to determine the degree of mite control as compared with untreated check plants. In such operations, each of the O-(6-chloro-2-pyridinyl) P-ethyl N-methylphosphonamidothioate, O-(6-chloro-2-pyridinyl) P-methyl N-methylphosphonamidothioate, O-(6-chloro-2-pyridinyl) P-ethylphosphonamidothioate, O-(6-fluoro-2-pyridinyl) P-ethyl N-methylphosphonamidothioate, O-(5-chloro-2-pyridinyl) P-ethyl N-methylphosphonamidothioate, O-(5-bromo-3,6-dichloro-2-pyridinyl) P-ethyl N-methylphosphonamidothioate, and O-(6-(trifluoromethyl)-2-pyridinyl) P-ethyl N-methylphosphonamidothioate.

Compounds were found to give 100% control of two-spotted spider mites at a concentration of 400 p.p.m.

EXAMPLE 3

A thin layer of a bean diet is placed in a container and covered with a thin layer of hot paraffin. When cooled, the wax surface is broken by penetrating the same with a circle of points mounted in a hot iron. The containers are then sprayed with an aqueous dispersion containing one of th active ingredients of the present invention at a concentration of 400 p.p.m. and a mass of Codling moth eggs are placed on the surface of the treated media. The containers are then maintained under conditions conducive to growth for a period of 6 days, after which they are examined. The degree of control obtained, as compared with controls, is determined by counting and recording the frass piles which are an indication of active larvae.

In such operations, each of the O-(6-chloro-2-pyridinyl) P-ethyl N-methylphosphonamidothioate, O-(6-chloro-2-pyridinyl) P-methyl N-methylphosphonamidothioate, O-(6-chloro-2-pyridinyl) P-ethylphosphonamidothioate, O-(6-fluoro-2-pyridinyl) P-ethyl N-methylphosphonamidothioate, O-(5-chloro-2-pyridinyl) P-ethyl N-methylphosphonamidothioate, O-(5-bromo-3,6-dichloro-2-pyridinyl) P-ethyl N-methylphosphonamidothioate, O-(6-(trifluoromethyl)-2-pyridinyl) P-ethyl N-methylphosphonamidothioate, and O-(3,5,6-trichloro-2-pyridinyl) P-ethyl N-methylphosphonamidothioate compounds were found to give 100% control of newly hatched Codling moth larvae.

The following representative forms for application of the active ingredients of the present invention further illustrate the present invention; where not otherwise expressly stated, "parts" means parts by weight. All percentages given therein are calculated on the total weight of the respective composition.

Dust — the following components are employed to produce a 10% dust:
    10 parts O-(6-chloro-2-pyridinyl) P-phenyl N-methylphosphonamidothioate,
    5 parts of finely dispersed silicic acid having a particle size of about 25 mμ and a density of about 2.2 (commercially available under the trademark "Aerosil"),
    85 parts talcum The active substance is mixed and milled with the carriers.

Wettable powders — the following ingredients are used to produce a 10% wettable powder:
    10 parts O-(5-chloro-2-pyridinyl) P-ethyl N-methylphosphonamidothioate,
    3 parts of a mixture of the sodium salts of saturated fatty alcohol sulphates,
    5 parts of sodium methylene-bis-naphthalene sulphonate,
    82 parts of Kaolin The active substances are intimately mixed with the carriers and dispersing agents in suitable mixers and the mixture is milled in corresponding mills and rollers. Wettable powders are obtained which can be diluted with water to form suspensions of any concentration desired.

Emulsion concentrate — to produce a 25% emulsion concentrate:

25 parts of O-(3,5,6-trichloro-2-pyridinyl) P-ethyl N-methylphosphonamidothioate,
2.5 parts of epichlorohydrin
5 parts of a composite emulsifier consisting of the condensation product of octylphenol and ethylene oxide (average molar ratio of 1:10) and calcium dodecylphenyl sulfonate, in a weight ratio of about 1:1
67.5 parts of xylene are mixed together. This concentrate can be diluted with water to form emulsions of concentrations suitable for the protection of plants.

The substituted 2-pyridinol, and phosphono-chloridate or chloridothioate reactants employed in preparing the active ingredients of the present invention are known and are available or can be prepared according to methods which are known or are analogous to those set forth in the open literature.

Although the invention is described with respect to specific modifications, the details thereof are not to be construed as limitations except to the extent indicated in the following claims.

What is claimed is:

1. A compound of the formula:

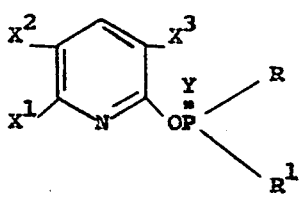

wherein
Y represents a chalcogen of atomic number 8 to 16, inclusive;
each $X^1$, $X^2$ and $X^3$ independently represents hydrogen, bromo, chloro, fluoro or trifluoromethyl, with the proviso that at least one of $X^1$, $X^2$ and $X^3$ is always other than hydrogen;
R represents an alkyl radical of 1 to 3 carbon atoms;
$R^1$ represents

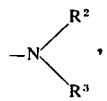

and
$R^2$ and $R^3$ each independently represent hydrogen, methyl or ethyl.

2. A compound according to claim 1 wherein R represents alkyl of 1 to 3 carbon atoms.

3. A compound according to claim 1 wherein at least one of $R^2$ and $R^3$ represents hydrogen.

4. A compound according to claim 2 wherein Y is a chalcogen of atomic number 16 and R, $X^2$ and $X^3$ each represent hydrogen.

5. A compound according to claim 4 wherein at least one of $R^2$ and $R^3$ is hydrogen.

6. A compound according to claim 1 selected from the group consisting of O-(6-chloro-2-pyridinyl) P-ethyl N-methylphosphonamidothioate, O-(6-chloro-2-pyridinyl) P-methyl N-methylphosphonamidothioate, O-(6-chloro-2-pyridinyl) P-ethylphosphonamidothioate, O-(6-fluoro-2-pyridinyl) P-ethyl N-methylphosphonamidothioate, O-(5-chloro-2-pyridinyl) P-ethyl N-methylphosphonamidothioate, O-(3,5,6-trichloro-2-pyridinyl) P-ethyl N-methylphosphonamidothioate, O-(5-bromo-3,6-dichloro-2-pyridinyl) P-ethyl N-methylphosphonamidothioate, and O-(6-(trifluoromethyl)-2-pyridinyl) P-ethyl N-methylphosphonamidothioate.

7. A compound according to claim 2 which is O-(6-chloro-2-pyridinyl) P-ethylphosphonamidothioate.

8. A compound according to claim 5 which is O-(6-chloro-2-pyridinyl) P-ethyl N-methylphosphonamidothioate.

9. A compound according to claim 5 which is O-(6-chloro-2-pyridinyl) P-methyl N-methylphosphonamidothioate.

10. A compound according to claim 5 which is O-(6-fluoro-2-pyridinyl) P-ethyl N-methylphosphonamidothioate.

11. A compound according to claim 5 which is O-(6-(trifluoromethyl)-2-pyridinyl) P-ethyl N-methylphosphonamidothioate.

12. A compound according to claim 3 which is O-(5-chloro-2-pyridinyl) P-ethyl N-methylphosphonamidothioate.

13. A compound according to claim 3 which is O-(3,5,6-trichloro-2-pyridinyl) P-ethyl N-methylphosphonamidothioate.

14. A compound according to claim 3 which is O-(5-bromo-3,6-dichloro-2-pyridinyl) P-ethyl N-methylphosphonamidothioate.

* * * * *